United States Patent [19]

Marciel

[11] Patent Number: Plant 6,583

[45] Date of Patent: Feb. 7, 1989

[54] ROSE PLANT NAMED DEVAURORA

[75] Inventor: Stanley G. Marciel, Pleasanton, Calif.

[73] Assignee: DeVor Nurseries, Inc., Pleasanton, Calif.

[21] Appl. No.: 70,730

[22] Filed: Jul. 7, 1987

[51] Int. Cl.[4] ..... A01H 5/00

[52] U.S. Cl. ..... Plt./7

[58] Field of Search ..... Plt./7

*Primary Examiner*—James R. Feyrer

*Attorney, Agent, or Firm*—Charles W. Rummler

[57] ABSTRACT

A new and distinct variety of miniature rose plant particularly distinguished by its small, bushy, upright form and its continuous year around profuse production of small, bright orange blossoms, characterized by having a light yellow central portion surrounded by orange-red petal coloration, the plant being particularly suited to pot plant culture for indoor growing, as well as being suitable for pot plant forcing for mass market production.

1 Drawing Sheet

BACKGROUND OF THE INVENTION

This new miniature rose plant originated as a seedling planted by me at Pleasanton, Calif., with seeds derived from a hybrid developed by my crossing 'Amber Flash' (U.S. Plant Pat. No. 5,271) with the variety 'Rhumba' (U.S. PlantPat. No. 1,919) as the pollen parent with the object of producing small, full, bushy plants for pot plant forcing with good continuous year around production of bright orange blooms and good for indoor growing. My new miniature rose variety seedling was selected by me for propagation and test because it appeared to possess the favorable qualities that I was seeking and the selected plant was propagated by me at Pleasanton, Calif., by means of cuttings; and several generations of this new plant have demonstrated that the favorable characteristics of the selected seedling would hold true from generation to generation and appeared to be firmly fixed.

DESCRIPTION OF THE DRAWING

My new miniature rose plant is illustrated by the accompanying photographic drawing, in which the upper view shows a fully grown potted plant of my new variety illustrating its bushy character as well as buds and flowers in various stages of opening. The lower view shows newly opened and fully opened face views of the flower together with front and back side views of typical leaves and a cutting illustrating a bud in an early stage of opening with a new leaf, the colors shown being as close to those herein specified as is reasonably possible to obtain by conventional photographic procedures.

DESCRIPTION OF THE NEW VARIETY

The following is a detailed description of my new miniature rose plant based upon observation of plants grown in greenhouse at Pleasanton, Calif., the color designations being according to The R.H.S. Colour Chart published by The Royal Horticultural Society of London, England.

THE PLANT

Origin: Seedling.

Parentage:

*Seed parent.*—'Amber Flash' (U.S. Plant Pat. No. 5,271).

*Pollen parent.*—'Rhumba' (U.S. Plant Pat. No. 1,919).

Classification:

*Botanic.*—Miniature Rose.

*Commercial.*—Mini Rose for Pot Forcing for Mass Market Production.

Form: Small, upright, free branching bush.

Growth: Vigorous and sturdy.

Height: 130 mm. in four inch pot at twelve week full bloom.

General coloration: Yellow Green, 144A.

Foliage:

*Quantity.*—Abundant.

*Numbers of leaves.*—About ten to twelve from hook on flower stems.

*Leaf size.*—Length — About 33 mm. with three leaflets and about 45 mm. with five leaflets.

*Leaflets.*—Size: About 22 mm. long. Shape: Oval with serrated margins.

*Texture.*—Mildly leathery.

*Aspect.*—Smooth and glossy.

*Color.*—Upper side — Green, 139B. Under side — Green, 138B.

*Stipules.*—Thread-like.

*Petiolule.*—Length: About 1 mm.

*Rachis.*—About 32 mm. long and smooth.

*Petioles.*—Length: About 8 mm.

*Ribs and veins.*—Prominently grooved on the top side of leaf.

Thorns:

*Number.*—Sparse.

*Size.*—About 5 mm.

*Color.*—Greyed Orange, 177B.

THE BUD

Form: Small and pointed.

*Diameter.*—About 5 mm.

*Length.*—About 7 mm.

Rate of opening: Moderately slow.

Color of petals:

*When sepals first divide.*—Orange Red, 34A.

*When petals begin to unfurl.*—Orange Red, 33A.

Sepals:

*Number.*—Five.

*Shape.*—Ovate with leafing, two small leaves on each side of the sepals.

*Character.*—Hooded over the bud. When flowers open, the sepals curl back.

*Color.*—Inside — Greyed Green, 191B. Outside — Greyed Green, 143A.

Calyx:

*Shape.*—Funnel-shaped.

*Size.*—Small.

*Splitting.*—The calyx does not split.

*Aspect.*—Slightly hairy.

Peduncle of flower stem:

*Length.*—About 32 mm.

*Character.*—Slender and erect.

*Color.*—Yellow Green, 144A.

THE FLOWER

Blooming habit: Continuous and profusely the year around, blooming freely under glass.

Size: Small.

*Diameter.*—26 mm.

*Depth.*—8 mm.

Borne: Singly.

Form: Cup-shaped when bloom first opens, becoming semi-flat when bloom matures.

Petalage:

*Number of petals.*—About fifteen to eighteen with two or three florets.

*Arrangement.*—Imbricated.

*Form.*—Generally oval with smooth, obtuse apex. The petal reflexes when the flower is fully open.

*Texture.*—Leathery.

*Appearance.*—Velvety.

*Color.*—Outer petals: Upper Side: Body — Orange Red, 33A. Base — Yellow, 13B. Color measurement — About 5 mm. for 33A and about 3 mm. for 13B. Reverse side: Body — Orange Red, 34A. Base — Yellow, 13C. Color measurement — About 5 mm. for 34A and about 3 mm. for 13C. Inside petals: Upper side: Body — Orange Red, 33A. Base — Yellow, 13B. Color measurement — About 4 mm. for 33A and about 2 mm. for 13B. Reverse side: Body — Orange Red, 34A. Base — Yellow, 13C. Color measurement — About 4 mm. for 33A and about 2 mm. for 13C.

*Petaloids.*—Number: Two or three. Size: About 4 mm. Color: Orange Red, 33A.

Discoloration after full bloom: The petal colors fade after several days to a pleasant pink tone and the yellow base turns white.

Persistence: The petals drop cleanly.

Fragrance: Slightly spicy.

Lasting quality: About ten to fourteen days on the plant.

Disease resistance: Moderately resistant to mildew, black spot and rust, as observed at Pleasanton, Calif.

REPRODUCTIVE ORGANS

Stamens:

*Number.*—About 47 to 50 in introrse arrangement.

*Anthers.*—Size: About 2 mm. Color: Yellow Orange, 22A.

*Filaments.*—Length: About 2 mm. Color: Yellow Orange, 22D.

*Pollen.*—Color: Yellow Orange, 22A.

Pistils:

*Number.*—About 20 to 25.

*Styles.*—Length: About 2.5 mm. Color: Yellow, 11C.

*Stigmas.*—Color: Yellow, 11C.

Character of ovaries: The styles are unattached to each other throughout the small funnel-shaped calyx tubes.

This new mini rose has small blooms but brilliant in color and the small, rounded, compact bush has shiny leaves, very pleasing in appearance.

I claim:

1. The new and distinct variety of miniature rose plant and parts thereof, substantially as herein shown and described, characterized by its profuse and continuous production of bright orange flowers of generally small size, and by its vigorous, upright and free branching growth habit.

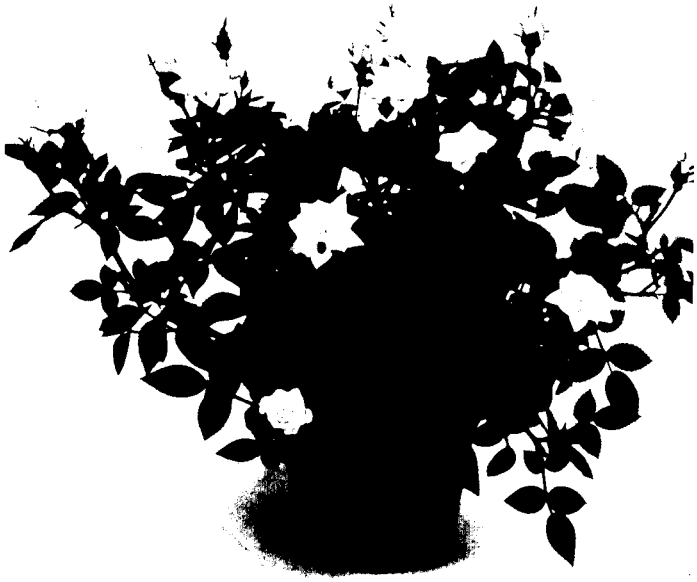
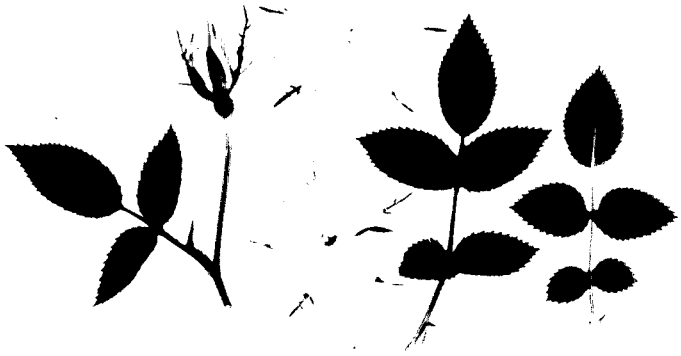

* * * * *